(12) United States Patent
Greiser et al.

(10) Patent No.: US 12,318,184 B2
(45) Date of Patent: Jun. 3, 2025

(54) MAGNETIC RESONANCE IMAGING OF AN ORGAN STRUCTURE

(71) Applicant: Siemens Healthcare GmbH, Erlangen (DE)

(72) Inventors: Andreas Greiser, Erlangen (DE); Venkata Veerendranadh Chebrolu, Rochester, MN (US); Boris Mailhe, Plainsboro, NJ (US); Mariappan S. Nadar, Plainsboro, NJ (US); Daniel Rinck, Forchheim (DE)

(73) Assignee: Siemens Healthineers AG, Erlangen (DE)

( * ) Notice: Subject to any disclaimer, the term of this patent is extended or adjusted under 35 U.S.C. 154(b) by 149 days.

(21) Appl. No.: 18/108,173

(22) Filed: Feb. 10, 2023

(65) Prior Publication Data
US 2023/0255506 A1   Aug. 17, 2023

Related U.S. Application Data

(60) Provisional application No. 63/310,788, filed on Feb. 16, 2022.

(51) Int. Cl.
*A61B 5/055* (2006.01)
*A61B 5/00* (2006.01)

(52) U.S. Cl.
CPC ............ *A61B 5/055* (2013.01); *A61B 5/0037* (2013.01); *A61B 2576/00* (2013.01)

(58) Field of Classification Search
None
See application file for complete search history.

(56) References Cited

U.S. PATENT DOCUMENTS

2015/0182117 A1* 7/2015 Senegas ............... G01R 33/543
                                                         600/410
2018/0025466 A1* 1/2018 Mazurkewitz ........ G06T 11/008
                                                         382/131
2019/0369181 A1* 12/2019 Chang .............. G01R 33/56572
(Continued)

FOREIGN PATENT DOCUMENTS

EP        3245532 A1    11/2017
WO     2016120086 A1     8/2016

OTHER PUBLICATIONS

Sénégas, Julien et al; "A Rigid Registration Method for Automated Scan Planning in Follow-Up Examinations: Retrospective Analysis From Volunteer And Patient Neuro Scans"; Proceedings of the international society for magnetic resonance in medicine; published: Apr. 21, 2012; XP040624989.

*Primary Examiner* — Joel Lamprecht
*Assistant Examiner* — Ashish S Jasani
(74) *Attorney, Agent, or Firm* — Banner & Witcoff Ltd.

(57) ABSTRACT

A method of scanning an organ structure of a patient using magnetic resonance imaging, includes scanning, in a first scanning process, the patient to obtain first image data indicative of at least the organ structure of the patient. The method further includes determining, based on the first image data, one or more parameters obtain second image data indicative of at least the organ structure of the patient. The first scanning process includes a first quality of imaging scan, the second scanning process includes a second quality of imaging scan, and the first quality of imaging scan is higher than the second quality of imaging scan.

12 Claims, 9 Drawing Sheets

(56) References Cited

U.S. PATENT DOCUMENTS

| | | | |
|---|---|---|---|
| 2020/0214619 A1* | 7/2020 | Leng | G06T 7/11 |
| 2020/0300957 A1* | 9/2020 | Chen | G01R 33/5608 |
| 2021/0080531 A1* | 3/2021 | Gui | A61B 5/7264 |
| 2021/0158514 A1 | 5/2021 | Greiser et al. | |
| 2021/0158948 A1 | 5/2021 | Greiser | |
| 2022/0409083 A1* | 12/2022 | Lyu | G01R 33/5611 |

* cited by examiner

MAGNETIC RESONANCE IMAGING OF AN ORGAN STRUCTURE

TECHNICAL FIELD

The disclosure relates in one aspect to a method of scanning an organ structure of a patient using magnetic resonance imaging. In another aspect, the disclosure relates to a method of scanning a patient using magnetic resonance imaging. In another aspect, the disclosure relates to a magnetic resonance imaging system.

BACKGROUND

Magnetic resonance imaging is a known imaging method in which magnetic resonance images of an interior of an examination target can be generated. For the performance of a magnetic resonance measurement, the scanning target is positioned in a strong, static and homogeneous basic magnetic field of a magnetic resonance imaging scanner. To trigger so-called nuclear magnetic resonances, radio-frequency excitation pulses are radiated into the scanning target. Every radio-frequency excitation pulse causes certain nuclear spins of the scanning target to deviate from the basic magnetic field by an amount that is also known as the flip angle. The excited nuclear spins can have a rotating and decaying magnetization (nuclear magnetic resonance) which can be detected by means of special antennas. Magnetic gradient fields can be superimposed on the basic magnetic field for spatial encoding of the nuclear magnetic resonances of the scanning target.

Received nuclear magnetic resonances are typically digitized and stored as complex values in a k-space matrix. This k-space matrix can be used as the basis for a reconstruction of magnetic resonance images and the determination of spectroscopy data. A magnetic resonance image is typically reconstructed by means of a multidimensional Fourier transform of the k-space matrix.

As magnetic resonance imaging does not utilize ionizing radiation, magnetic resonance imaging is suitable for continuous diagnostic monitoring of a patient in the context of a longitudinal imaging study. Longitudinal imaging studies usually entail a plurality of imaging scans in order to determine the progression of a disease or the outcome of therapeutic treatment over a predetermined duration. However, magnetic resonance imaging can take longer to perform than other known imaging techniques. Reduced duration magnetic resonance imaging scans may not be able to achieve the image quality needed when scanning a patient. The length of time associated with the acquisition of magnetic resonance data can also be a problem when treating a large number of patients.

SUMMARY

It is therefore an object of the disclosure to improve the efficiency of imaging of a scanning target, in particular a patient or an organ structure of a patient, and in some specific examples a prostate of a patient.

This object is achieved according to the independent claims herein. The dependent claims are related to further aspects of the disclosure.

The disclosure relates in one aspect to a method of scanning an organ structure of a patient using magnetic resonance imaging. An organ structure may comprise a collection of tissues joined in a structural unit to serve a common function. Examples of organ structures are a liver, a prostate, an eye, a brain, an intestine, a breast, a heart, but also pathologies related to such organ structures, particularly tumors, cancerous tissue, and the like. In the following, the scanning of a prostate will be used as an exemplary application. However, it is to be understood that the disclosure is not limited to scanning of a prostate and may relate to scanning of others organ structures, but also objects.

The method comprising; scanning, in a first scanning process, the patient to obtain first image data indicative of at least the prostate of the patient; determining, based on the first image data, one or more parameters of a second scanning process to be performed on the patient; and scanning the patient in the second scanning process to obtain second image data indicative of at least the prostate of the patient, wherein the first scanning process comprises a first quality of imaging scan, the second scanning process comprises a second quality of imaging scan, and the first quality of imaging scan is higher than the second quality of imaging scan.

By utilizing the first image data to determine one or more parameters of the second scanning process, a volume of data required to be obtained by the second scanning process may be reduced in comparison to a method where first image data is not used to determine one or more parameters of a second scanning process. For example the data required from the second scanning process can be constrained using the first image data. Reduction of the amount of data required to be obtained by the second scanning process may enable use of a lower quality imaging scan in the second scanning process, which may reduce a time taken to perform the second scanning process in comparison to a time taken to perform the first scanning process. This can lead to increased efficiency for a longitudinal imaging study comprising the first and second scanning processes, and may find particular utility in a longitudinal imaging study of a prostate of a patient.

The first scanning process may be performed using a first magnetic resonance imaging scanner, and the second magnetic resonance imaging process may be performed using a second magnetic resonance imaging scanner different to the first magnetic resonance imaging scanner. This may enable the second magnetic resonance imaging scanner to be of lower cost and/or quality than the first magnetic resonance imaging scanner.

The method may comprise determining, based on a property of the second magnetic resonance imaging scanner, one or more parameters of the second scanning process. Taking account of the properties of the second magnetic resonance imaging when determining one or more parameters to be utilized in the second scanning process may constrain the data required to be obtained in the second scanning process, and may facilitate determination of more optimized scanning parameters to be utilized in the second scanning process. The one or more parameters determined based on the property of the second magnetic resonance imaging scanner may comprise the same one or more parameters of the second scanning process that is determined based on the first image data. The one or more parameters determined based on the property of the second magnetic resonance imaging scanner may comprise a further one or more parameters of the second scanning process to the one or more parameters of the second scanning process that is determined based on the first image data.

The one or more parameters of the second scanning process may comprise any one or more of a spatial resolution of the second scanning process, a signal-to-noise ratio of the second scanning process, an imaging volume of the second scanning process, a slice thickness of the second scanning process, and a volume of sample recording of nuclear magnetic resonances of the second scanning process.

The first quality of imaging scan may comprise any one or more of a greater spatial resolution than the second quality of imaging scan, a greater signal-to-noise ratio than the second quality of imaging scan, a greater imaging volume than the second quality of imaging scan, a lower slice thickness to be resolved than the second quality of imaging scan, and a higher volume of sample recording of nuclear magnetic resonances compared to the second quality of imaging scan. Choosing parameters in such a manner may provide the second quality of imaging scan with a reduced quality relative to the first quality of imaging scan used in the first scanning process, which may facilitate a reduction in the amount of data required to be obtained in the second scanning process.

The method may comprise determining the one or more parameters of the second scanning process based on the quality of the first scanning process. For example, as the first quality of imaging scan is relatively high, the one or more parameters of the second scanning process can be chosen such that the second quality of imaging scan is relatively low.

The method may comprise determining the one or more parameters of the second scanning process based on one or more parameters of the first scanning process associated with the first image data. For example, when the first image data is obtained with a relatively high spatial resolution, a relatively low spatial resolution may be determined for the second scanning process. When the first image data is obtained with a relatively high signal-to-noise ratio, a relatively low signal-to-noise ratio may be determined for the second scanning process. When the first image data is obtained with a relatively high imaging volume, a relatively low imaging volume may be determined for the second scanning process. When the first image data is obtained with a relatively low slice thickness to be resolved, a relatively high slice thickness to be resolved may be determined for the second scanning process. When the first image data is obtained with a relatively high volume of sample recording of nuclear magnetic resonances, a relatively low volume of sample recording of nuclear magnetic resonance may be determined for the second scanning process.

The method may comprise determining a region of interest in the first image data, and determining, based on the determined region of interest, the one or more parameters of the second scanning process. This may help to reduce an amount of data required to be obtained by the second scanning process, for example by constraining data required to be obtained in the second scanning process to data corresponding to the region of interest in the first image data and/or by enabling data not corresponding to the region of interest to be obtained at a reduced quality relative to the data corresponding to the region of interest. The region of interest may correspond substantially to the prostate of the patient.

Determining the region of interest may comprise performing a segmentation process on the first image data. This may facilitate the identification of a perimeter of a target anatomy of the patient, for example the prostate of the patient, as the region of interest. This may enable data to be obtained in the second scanning process to be constrained to be data corresponding to the prostate of the patient.

The segmentation process may comprise an automatic segmentation process. This may provide greater efficiency than, for example, a manual segmentation process carried out by an operator of the first magnetic resonance imaging scanner.

Determining the region of interest may comprise identifying at least one of a landmark in the first image data and a sub-compartment in the first image data. Identifying a landmark in the first image data, for example a landmark within a region of the first image data corresponding to a landmark within the prostate of the patient, may enable data to be obtained in the second scanning process to be constrained to a region including the landmark. The landmark may correspond to a region of the prostate to be treated in a treatment process. Identifying a sub-compartment in the first image data, for example a sub-compartment within a region of the first image data corresponding to a sub-compartment within the prostate of the patient, may enable data to be obtained in the second scanning process to be constrained to a region including the sub-compartment. The sub-compartment may comprise sub-compartment that includes a landmark within the first image data. The sub-compartment may correspond to a region of the prostate to be treated in a treatment process.

Determining the parameter of the second scanning process may comprise determining the parameter of the second scanning process to modify a point spread function associated with the region of interest. This may assist with modification of spatial encoding in the second scanning process. Modifying the point spread function associated with the region of interest may comprise increasing a peak of the point spread function associated with the region of interest.

Determining the parameter of the second scanning process may comprise determining the parameter of the second scanning process to modify spatial encoding in the second scanning process. This may improve efficiency of the second scanning process relative to a method where the parameter of the second scanning process is not determined, based on the first image data, to modify spatial encoding in the second scanning process.

The method may comprise, prior to determining the one or more parameters of the second scanning process, performing a localizer scan on the patient to obtain localizer data, comparing the first image data to the localizer data to determine a consistency metric between the first data and the localizer data, and when the consistency metric is above a threshold value, determining the one or more parameters of the second scanning process and scanning the patient in the second scanning process. Localizer scans may be relatively quick in comparison to a full scanning process such as the first scanning process performed by the first magnetic resonance imaging scanner, and so may be performed without detrimentally impacting the efficiency of a longitudinal imaging study. By comparing the first image data to the localizer data to determine the consistency metric between the first data and the localizer data, and proceeding to the second scanning process when the consistency metric is above the threshold value, the second scanning process may only be performed where the localizer data matches the first image data to a sufficient degree that the reduced level of data to be obtained in the second scanning process can be trusted. The localizer scan may be performed using the second magnetic resonance imaging scanner.

Comparing the first image data to the localizer data to determine the consistency metric may comprise utilizing a sum of squared difference between pixels in the localizer data and the first image data. Other appropriate measures for distance between the localizer data and the first image data are envisaged.

The first image data may comprise initial localizer data obtained in an initial localizer scan performed by the first magnetic resonance imaging scanner, and the method may comprise comparing the initial localizer data obtained from the first magnetic resonance imaging scanner to the localizer data obtained from the second magnetic resonance imaging scanner, to determine the consistency metric.

The method may comprise, when the consistency metric is below the threshold value, scanning the patient in a re-scanning process comprising a quality of imaging scan substantially similar to the first quality of imaging scan, to obtain updated first image data indicative of at least the prostate of the patient. This may ensure that relatively high quality scans are performed where changes relative to an initial relatively high quality scan are identified, and may help to ensure that the second scanning process, where relatively low quality image data is obtained, can be trusted. The re-scanning process may be performed using the first magnetic resonance imaging scanner, or a further magnetic resonance imaging scanner configured to perform a quality of imaging scan substantially similar to the first quality of imaging scan.

The method may comprise, prior to performing the re-scanning process, providing an indication that the re-scanning process is required. The method may comprise providing the indication at a user interface associated with the second magnetic resonance imaging scanner.

The method may comprise reconstructing the second image data based on the first image data. This may improve quality of images obtained relative to a method where the second image data alone is utilized to obtain an image. Accordingly, such reconstruction may obviate the need for the second scanning process to be of high quality, thereby enabling one or more parameters of the second scanning process to be determined so that the quality of the second scanning process is lower than the quality of the first scanning process.

The method may comprise reconstructing the second image data based on a dataset comprising data relating to previously scanned patients, for example patients other than the patient that has been scanned in the second scanning process. This may improve quality of images obtained relative to a method where the second image data alone is utilized to obtain an image. The method may comprise utilizing a machine learning model, for example a neural network, to reconstruct the second image data.

The method may comprise determining, based on a status of the prostate of the patient, one or more parameters of the second scanning process. Taking account of the status of the prostate, for example a status of disease of the prostate, when determining one or more parameters to be utilized in the second scanning process may constrain the data required to be obtained in the second scanning process, and may facilitate determination of optimal scanning parameters to be utilized in the second scanning process.

The one or more parameters of the second scanning process may comprise an intended location of a patient relative to the second magnetic resonance imaging scanner. This may help to constrain the data required to be obtained in the second scanning process. An intended location of a patient relative to the second magnetic resonance imaging scanner can be determined based on the determined region of interest in the first image data.

The method may comprise determining, based on at least one of the first image data and the second image data, one or more parameters of a third scanning process to be performed on the patient; and scanning the patient in the third scanning process to obtain third image data indicative of at least the prostate of the patient. The third scanning process may form part of a longitudinal imaging study, and may facilitate ongoing monitoring of the prostate of the patient. The third scanning process may comprise the re-scanning process previously described. The third scanning process may be performed using a third magnetic resonance imaging scanner.

The third scanning process may comprise a re-scanning process, for example performed using the first magnetic resonance imaging scanner, or a further magnetic resonance imaging scanner configured to perform a quality of imaging scan substantially similar to the first quality of imaging scan performed by the first magnetic resonance imaging scanner. The re-scanning process may be triggered by any of a length of time since the first scanning process, a pre-determined number of subsequent scans that have taken place since the first scanning process, and a pre-determined number of treatments on the patient that have taken place since the first scanning process.

The third scanning process may comprise a third quality of imaging scan, and the first quality of imaging scan may be higher than the third quality of imaging scan. The third quality of imaging scan may be substantially similar to the second quality of imaging scan.

The third magnetic resonance imaging scanner may comprise a different magnetic resonance imaging scanner to the first magnetic resonance imaging scanner. The third magnetic resonance imaging scanner may be configured to perform a third quality of imaging scan in the third scanning process, and the first quality of imaging scan may be higher than the third quality of imaging scan.

The method may comprise comparing the second image data to the first image data to identify a change, for example a structural and/or functional change, between the first image data and the second image data, performing a quantitative analysis based on the identified change, and determining the parameter of the third scanning process based on the quantitative analysis. The method may comprise comparing at least one of the first image data and the second image data with the third image data to identify a change between the third image data and the respective first and/or second image data. The change may comprise an intended change and/or an unintended change, for example with the change taking place as a result of treatment or the lack thereof.

The method may comprise transmitting the first image data from a magnetic resonance imaging scanner that performs the first scanning process to a remote processing system, for example remote from the magnetic resonance imaging scanner that performs the first scanning process, and determining the parameter of the second scanning process using the remote processing system. This may reduce a computing requirement on the magnetic resonance imaging scanner that performs the first scanning process. The method may comprise transmitting the parameter of the second scanning process from the remote processing system to the magnetic resonance imaging scanner that performs the second scanning process. The remote processing system may comprise a cloud-based processing system. The method may comprise processing the first image data at the remote processing system to determine the region of interest in the first image data.

The method may comprise transmitting the first image data from the first magnetic resonance imaging scanner to a remote processing system, for example remote from the first magnetic resonance imaging scanner, and determining the parameter of the second scanning process using the remote processing system. This may reduce a computing requirement on the first magnetic resonance imaging scanner. The method may comprise transmitting the parameter of the second scanning process from the remote processing system to the second magnetic resonance imaging scanner. The remote processing system may comprise a cloud-based processing system. The method may comprise processing the first image data at the remote processing system to determine the region of interest in the first image data.

The method may comprise utilizing the second image data as part of a treatment process performed on the prostate of the patient. The treatment process may be performed substantially concurrently with the second scanning process. This may enable sufficient detail to be obtained to guide the treatment process, whilst reducing cost and/or complexity of the second scanning process relative to the first scanning process. The treatment process may comprise a guided radiotherapy process.

A further aspect of the present disclosure provides a magnetic resonance imaging system comprising: a first magnetic resonance imaging scanner configured to obtain, as part of a first scanning process, first image data indicative of at least a prostate of a patient, the first magnetic resonance imaging scanner configured to perform a first quality of imaging scan in the first scanning process; a second magnetic resonance imaging scanner different to the first magnetic resonance imaging scanner, the second magnetic resonance imaging scanner configured to obtain, as part of a second scanning process, second image data indicative of at least the prostate of the patient, the second magnetic resonance imaging scanner configured to perform a second quality of imaging scan in the second scanning process; and a processor configured to determine, based on the first image data, one or more parameters of the second scanning process; wherein the first quality of imaging scan is higher than the second quality of imaging scan.

A further aspect of the present disclosure provides a method of scanning a patient using magnetic resonance imaging, the method comprising; scanning the patient in a first scanning process to obtain first image data; scanning the patient in a localizing scanning process to obtain localizer data; comparing the first image data to the localizer data to determine a consistency metric between the first image data and the localizer data; when the consistency metric is above a threshold value: determining, based on the first image data, one or more parameters of a second scanning process to be performed on the patient; and scanning the patient in the second scanning process to obtain second image data, and when the consistency metric is below the threshold value: scanning the patient in a re-scanning process comprising a quality of imaging scan substantially similar to a quality of imaging scan, to obtain updated first image data.

A further aspect of the present disclosure provides a magnetic resonance imaging system comprising: a first magnetic resonance imaging scanner configured to obtain, as part of a first scanning process, first image data, the first magnetic resonance imaging scanner configured to perform a first quality of imaging scan in the first scanning process; a second magnetic resonance imaging scanner different to the first magnetic resonance imaging scanner, the second magnetic resonance imaging scanner configured to: obtain, in a localizing process, localization data; and obtain, as part of a second scanning process, second image data, the second magnetic resonance imaging scanner configured to perform a second quality of imaging scan in the second scanning process; and a processor configured to compare the first image data to the localizer data to determine a consistency metric between the first data and the localizer data, and: when the consistency metric is above a threshold value: determine, based on the first image data, one or more parameters of the second scanning process; and when the consistency metric is below the threshold value: provide an indication that a re-scanning process is required to obtain updated first image data.

In a preferred aspect, the disclosed magnetic resonance imaging system is configured to perform a method according to an aspect described above. Optional features of the aspects of the present disclosure may be equally applied to other aspects of the present disclosure, where appropriate.

According to an aspect, the magnetic resonance imaging system is configured for determining and/or adjusting a parameter of the first scanning process based on a property of the second magnetic resonance imaging scanner.

For example, the second magnetic resonance imaging scanner may have limited or extended imaging capabilities in comparison to the first magnetic resonance imaging scanner. Particularly, the second magnetic resonance imaging scanner may offer a limited field of view (or imaging volume), a limited spatial resolution, a limited gradient performance, a limited magnetic field strength, or the like. The parameter of the first scanning process may be determined in such a way to account or compensate for certain restrictions of the second magnetic resonance imaging scanner and/or to harmonize the first scanning process and the second scanning process.

Determining and/or adjusting the parameter of the first scanning process based on the property of the second scanning process may be a dedicated step of a method according to an aspect described above. Preferably, determining and/or adjusting the parameter of the first scanning process is carried out automatically via a processing unit and/or control unit of the first magnetic resonance imaging system. For this purpose, the processing unit and/or control unit may have access to a network and/or data base comprising information on the second magnetic resonance imaging scanner.

In providing a magnetic resonance imaging system, a process of acquiring magnetic resonance imaging data from an organ structure of a patient via multiple magnetic resonance imaging scanners, i. e. in a longitudinal imaging study, may favorably be facilitated and/or improved.

BRIEF DESCRIPTION OF THE DRAWINGS

The disclosure will be illustrated below with reference to the accompanying figures using example aspects. The illustration in the figures is schematic and highly simplified and not necessarily to scale.

DETAILED DESCRIPTION

Figure 1:
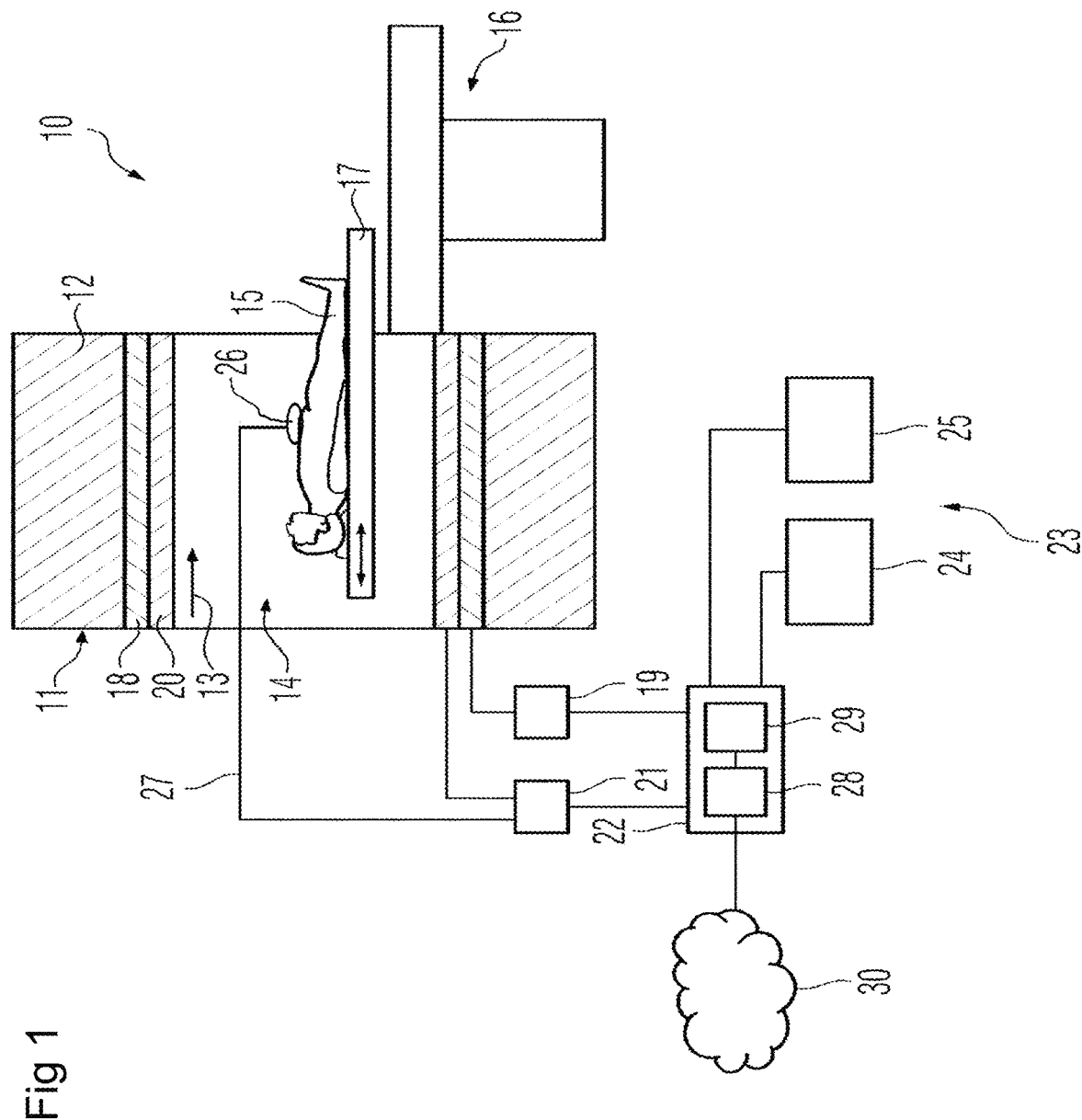
FIG. 1 is a schematic view of a magnetic resonance imaging scanner.

A magnetic resonance imaging scanner 10 according to the disclosure is illustrated schematically in FIG. 1. The magnetic resonance imaging scanner 10 comprises a magnet unit 11 comprising any of a permanent magnet, an electromagnet or a superconducting main magnet 12 for generating a strong and homogeneous main magnetic field 13. The magnetic resonance imaging scanner 10 also includes a patient-receiving region 14 for receiving a patient. In the present exemplary aspect, the patient-receiving region 14 is cylindrical and surrounded by the magnet unit 11 in a circumferential direction. However aspects of the patient-receiving region 14 that differ from this example are also envisaged.

The patient can be positioned in the patient-receiving region 14 by means of a patient support apparatus 16 of the magnetic resonance imaging scanner 10. For this purpose, the patient support apparatus 16 comprises a patient table 17 that can be moved within the patient-receiving region 14.

The magnet unit 11 comprises a gradient coil 18 for generating magnetic gradient fields used for spatial encoding during imaging. The gradient coil 18 is actuated by means of a gradient control unit 19 of the magnetic resonance imaging scanner 10. The magnet unit 11 also comprises a radio-frequency antenna illustrated here as a body coil 20 permanently integrated in the magnetic resonance imaging scanner 10. The body coil 20 is designed to excite nuclear spins located in the main magnetic field 13 generated by the main magnet 12. The body coil 20 is actuated by a radio-frequency unit 21 of the magnetic resonance imaging scanner 10 and radiates radio-frequency excitation pulses into an image-recording region substantially formed by a patient-receiving region 14 of the magnetic resonance imaging scanner 10. The body coil 20 is configured to receive nuclear magnetic resonances.

To control the main magnet 12, the gradient control unit 19, and the radio-frequency unit 21, the magnetic resonance imaging scanner 10 comprises a control unit 22. The control unit 22 is configured to control the performance of a sequence, such as, for example, an imaging GRE (gradient echo) sequence, a TSE (turbo spin echo) sequence or a UTE (ultra-short echo time) sequence. The control unit 22 also includes a computing unit 28 for evaluating magnetic resonance data acquired during a magnetic resonance measurement. The computing unit 28 of the magnetic resonance imaging scanner 10 is configured to use reconstruction methods in order to reconstruct magnetic resonance images on the basis of the magnetic resonance data. The computing unit 28 is connected to a storage unit 29 and a cloud storage 30. The computing unit is configured to store data such as, for example, magnetic resonance images, and magnetic resonance data on the storage unit 29 and the cloud storage 30, and retrieve this data from this storage unit or the cloud storage by means of a suitable interface. It is also conceivable, by means of a suitable application, for the patient 15 to use a mobile device (not shown) to access a storage region containing magnetic resonance images of the patient 15. Accordingly, the software application can be configured to output the magnetic resonance images on a screen of the mobile device.

The magnetic resonance imaging scanner 10 also includes a user interface 23 with a signal connection to the control unit 22. Control information, such as, for example, imaging parameters, but also reconstructed magnetic resonance images, can be displayed on a display unit 24, for example, on at least one monitor, of the user interface 23 for a user. Furthermore, the user interface 23 comprises an input unit 25 by means of which parameters of a magnetic resonance measurement can be input by the user.

The magnetic resonance imaging scanner 10 can further comprise a local receiving antenna 26 positioned on a relevant portion of the patient 15, for example overlying a region of the patient 15 expected to contain the prostate of the patient 15. The local receiving antenna 26 acquires nuclear magnetic resonances of the prostate of the patient 15 and transmits them to the computing unit 28 of the control unit 22. The local receiving antenna 26 comprises an electrical connecting lead 27 providing a signal connection to the radio-frequency unit 21 and the control unit 22. Like the body coil 20, the local receiving antenna 26 can also be embodied to excite nuclear spins and receive nuclear magnetic resonances. For this purpose, the local receiving antenna 26 can in particular have a drum-shaped structure enclosing a region of the patient 15. To emit radio-frequency excitation pulses, the local receiving antenna 26 is actuated by the radio-frequency unit 21.

The magnetic resonance imaging scanner 10 depicted can include further components usually comprised by magnetic resonance imaging scanners. It is also conceivable that instead of a cylindrical structure, the magnetic resonance imaging scanner 10 can have a C-shaped, triangular or asymmetrical structure of the magnetic-field-generating components. The magnetic resonance imaging scanner 10 can in particular be embodied to perform a magnetic resonance examination of a standing or seated patient 15. It is further conceivable for the magnetic resonance imaging scanner 10 to be specially embodied to perform imaging examinations of the prostate of a patient 15.

The magnetic resonance imaging scanner 10 illustrated in FIG. 1 can be used in the present disclosure as part of a longitudinal imaging study, and may find particular efficacy in a longitudinal imaging study of a prostate of the patient 15.

Figure 2:
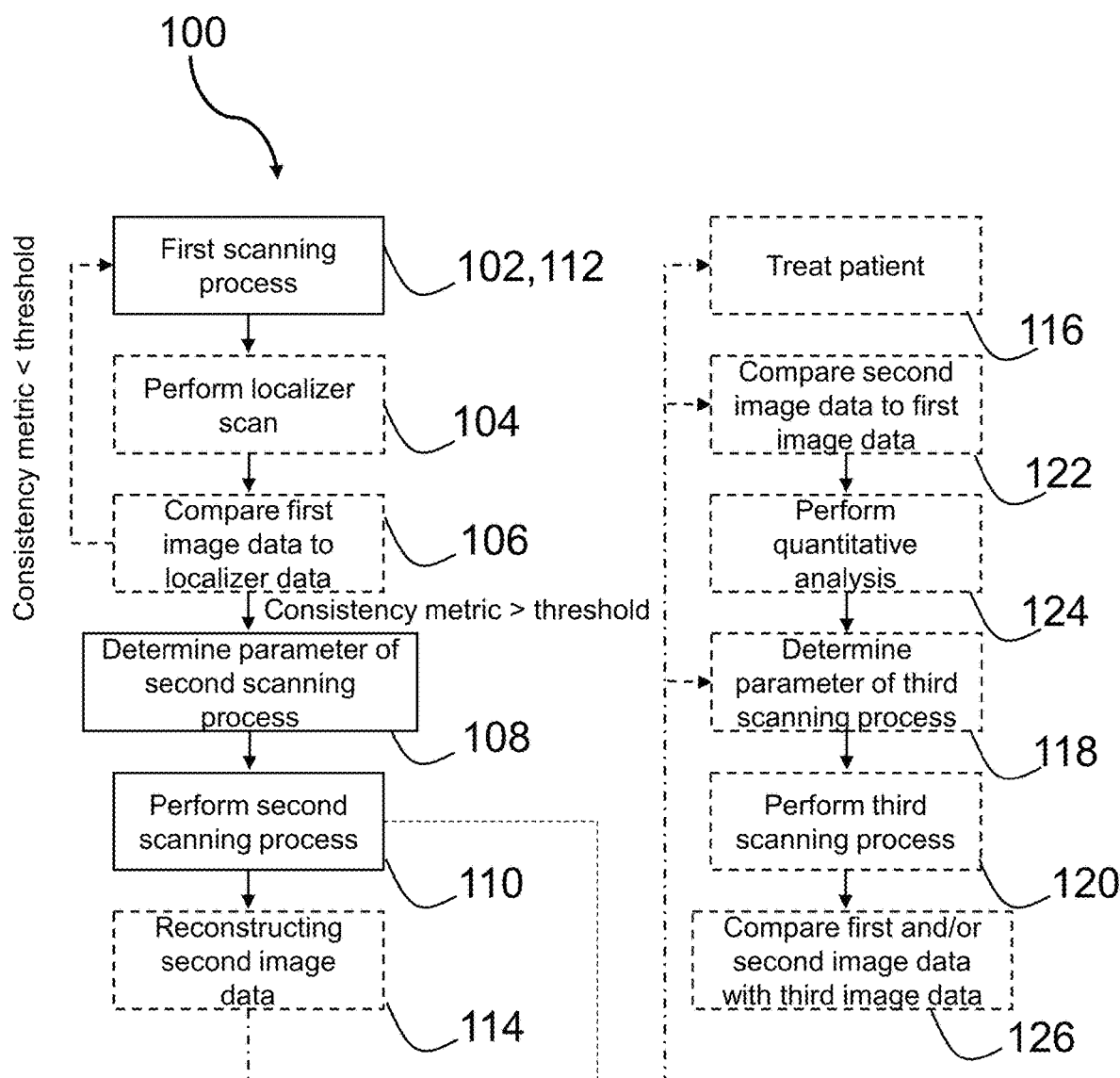
FIG. 2 is a flow diagram of a first method according to the present disclosure.

A first method 100 in accordance with the present disclosure is illustrated in the flow diagram of FIG. 2.

The method 100 comprises scanning 102, in a first scanning process, the patient 15 to obtain first image data indicative of at least the prostate of the patient, and the first scanning process comprises a first quality of imaging scan. The magnetic resonance imaging scanner 10 can be used to perform the first scanning process. In particular, the patient 15 can be placed on the patient table 17 and moved into the patient-receiving region 14. The magnet unit 11 and the local receiving antenna 26 can then be utilized to obtain the first image data in the form of magnetic resonance data.

The method 100 comprises optional steps of performing 104 a localizer scan on the patient to obtain localizer data, and comparing 106 the first image data to the localizer data to determine a consistency metric between the first data and the localizer data. In some aspects, performing 104 the localizer scan comprises utilizing the magnetic resonance imaging scanner 10.

In some aspects, comparing 106 the first image data to the localizer data to determine the consistency metric comprises utilizing a sum of squared difference between pixels in the localizer data and the first image data. Other appropriate measures for distance between the localizer data and the first image data are envisaged. The consistency metric can, for example, comprise a percentage similarity between the localizer data and the first image data, although other forms of consistency metric are also envisaged. In some examples, the first image data comprises initial localizer data obtained in an initial localizer scan performed as part of the first scanning process, and the initial localizer data is compared to the localizer data to determine the consistency metric.

When the consistency metric is above a threshold value, or indeed where the optional steps of performing 104 the localizer scan and comparing 106 the first image data to the localizer data are not performed, the method 100 comprises determining 108, based on the first image data, one or more parameters of a second scanning process SSP to be performed on the patient 15. Such determination 108 can take place using a region of interest in the first image data, as will be described in more detail hereafter.

The method 100 then comprises scanning 110 the patient in the second scanning process SSP to obtain second image data indicative of at least the prostate of the patient 15, and the second scanning process comprises a second quality of imaging scan. The first quality of imaging scan is higher than the second quality of imaging scan. The magnetic resonance imaging scanner 10 can be used to perform the second scanning process, in a similar manner to that described above for the first scanning process.

By utilizing the first image data to determine one or more parameters of the second scanning process, a volume of data required to be obtained by the second scanning process may be reduced in comparison to a method where first image data is not used to determine one or more parameters of a second scanning process. For example the data required from the second scanning process can be constrained using the first image data. Reduction of the amount of data required to be obtained by the second scanning process may enable use of a lower quality imaging scan in the second scanning process, which may reduce a time taken to perform the second scanning process in comparison to a time taken to perform the first scanning process. This can lead to increased efficiency for a longitudinal imaging study comprising the first and second scanning processes, and may find particular utility in a longitudinal imaging study of a prostate of a patient.

When the consistency metric is below the threshold value, the method 100 can comprise scanning 112 the patient in a re-scanning process comprising a quality of imaging scan substantially similar to the first quality of imaging scan, to obtain updated first image data. This may ensure that relatively high quality scans are performed where changes relative to an initial relatively high quality scan are identified, and may help to ensure that the second scanning process, where relatively low quality image data is obtained, can be trusted. The re-scanning process may be performed using the magnetic resonance imaging scanner 10. Prior to performing the re-scanning process, an indication can be provided that the re-scanning process is required. The indication can be provided at the user interface 23.

It will be appreciated that the first scanning process described above takes place prior to the second scanning process. A time between the first and second scanning processes can comprise any of minutes, hours, days, months, or years.

It will further be appreciated that a variety of parameters of the second scanning process can be determined based on the first image data. In some aspects, the one or more parameters of the second scanning process comprise any one or more of a spatial resolution of the second scanning process, a signal-to-noise ratio of the second scanning process, an imaging volume of the second scanning process, a slice thickness of the second scanning process, a volume of sample recording of nuclear magnetic resonances of the second scanning process, and a location of a patient in a magnetic resonance imaging scanner that performs the second scanning process.

Accordingly, in some aspects the first quality of imaging scan comprises any one or more of a greater spatial resolution than the second quality of imaging scan, a greater signal-to-noise ratio than the second quality of imaging scan, a greater imaging volume than the second quality of imaging scan, a lower slice thickness to be resolved than the second quality of imaging scan, and a higher volume of sample recording of nuclear magnetic resonances compared to the second quality of imaging scan.

In some aspects, the method comprises determining the one or more parameters of the second scanning process based on the quality of the first scanning process. For example, as the first quality of imaging scan is relatively high, the one or more parameters of the second scanning process can be chosen such that the second quality of imaging scan is relatively low.

In some aspects, method comprises determining the one or more parameters of the second scanning process based on one or more parameters of the first scanning process associated with the first image data. For example, when the first image data is obtained with a relatively high spatial resolution, a relatively low spatial resolution may be determined for the second scanning process. When the first image data is obtained with a relatively high signal-to-noise ratio, a relatively low signal-to-noise ratio may be determined for the second scanning process. When the first image data is obtained with a relatively high imaging volume, a relatively low imaging volume may be determined for the second scanning process. When the first image data is obtained with a relatively low slice thickness to be resolved, a relatively high slice thickness to be resolved may be determined for the second scanning process. When the first image data is obtained with a relatively high volume of sample recording of nuclear magnetic resonances, a relatively low volume of sample recording of nuclear magnetic resonance may be determined for the second scanning process.

As indicated previously, determining 104, based on the first image data, one or more parameters of the second scanning process to be performed on the patient 15 can take place based on a region of interest in the first image data. Use of such a region of interest can constrain data to be obtained in the second scanning process, enabling the second scanning processing to have a lower image quality than the first scanning process.

In some aspects, determining the region of interest in the first image data, for example determining the location of the prostate in the first image data, can comprise any of performing a segmentation process on the first image data, identifying a landmark in the first image data, and identifying a sub-compartment in the first image data. Details of processes for segmentation, for example automatic segmentation, of the first image data, and identification of landmarks and/or sub-compartments in the first image data, are not pertinent to the resent disclosure, and so will not be described further for sake of brevity.

Aspects where other details are utilized to determine parameters of the second scanning process are also envisaged.

In some aspects, a status of the prostate or other target anatomy of the patient 15, can be utilized in the determination of the parameters of the second scanning process. Such a status can include a status of disease of the prostate, and/or a treatment plan associated with the prostate.

Determination of parameters of the second scanning process can take place at the computing unit 28. In some aspects, determination of parameters of the second scanning process can take place remotely from the magnetic resonance imaging scanner 10, for example with processing taking place in the cloud or at some other remote computing system. Similar processing locations may be utilized for processing the first image data.

The method 100 also comprises an optional step of reconstructing 114 the second image data. Such reconstruction can take place based on the first image data, and/or based on a larger dataset containing data relating to other patients that have previously been scanned. It will be appreciated that known reconstruction processes may be utilized, and details of such reconstruction methods are not provided here for sake of brevity. Reconstructing 114 the second image data can take place at the magnetic resonance imaging scanner 10, or remotely such as in the cloud.

In some aspects, the second image data and/or a reconstruction of the second image data can be used in real-time as part of a guided treatment process, and hence the method 100 can comprise an optional step of treating 116 the patient 15 based on the second image data and/or a reconstruction of the second image data. For example, a guided radiotherapy treatment process can be performed on the patient based on the second image data and/or a reconstruction of the second image data.

In some aspects, the method 100 can include further optional steps of determining 118 based on at least one of the first image data and the second image data, one or more parameters of a third scanning process to be performed on the patient, and scanning 120 the patient in the third scanning process to obtain third image data indicative of at least the prostate of the patient. These steps can form part of a longitudinal imaging study, with such a longitudinal imaging study illustrated schematically in FIG. 3. Here relatively longer, high quality, scans are performed, with relatively shorter, lower quality, scans taking place between the relatively longer, high quality, scans. Determining parameters of the third scanning process can take place in a similar manner to determination of parameters of the second scanning process previously described. The magnetic resonance imaging scanner 10 can be used to perform the second scanning process, in a similar manner to that described above for the first scanning process.

The third scanning process can be performed with a similar or lower quality of imaging scan to the quality of imaging scan of the second scanning process. This may reduce a time taken to perform the third scanning process in comparison to a time taken to perform the first scanning process, which can lead to increased efficiency for the longitudinal imaging study. Alternatively, the third scanning process can be performed with a similar quality of imaging scan to the quality of imaging scan of the first scanning process. The third scanning process can then be thought of as a re-scanning process, or a re-learning process, where relatively high quality image data can be obtained to ensure that relatively low quality image data subsequently obtained as part of the longitudinal imaging study can be trusted.

Performance of a third scanning process that has a relatively high image quality can be triggered in a number of ways. In some aspects, a relatively high quality scanning process can be triggered in a longitudinal imaging study after a pre-determined number of imaging scans have been performed, or after a pre-determined time period has elapsed.

In some aspects, the scanning 120 of the patient in the third scanning process can be the same process as scanning 112 the patient in the re-scanning process previously described, and the third imaging process can then be triggered based on the consistency metric.

In some aspects, performance of the third scanning process can be triggered based on differences between the second image data and the first image data. For example, prior to determining 118 the one or more parameters of the third scanning process and scanning 120 the patient in the third scanning process, the method 100 can comprise optional steps of comparing 122 the second image data to the first image data to identify a change between the first image data and the second image data, performing 124 a quantitative analysis based on the identified change. Determining 118 the one or more parameters of the third scanning process can then take place based on the quantitative analysis. The change can comprise a structural and/or functional change between the first image data and the second image data.

In some aspects, the method 100 comprises a further optional step of comparing 126 at least one of the first image data and the second image data with the third image data to identify a change between the third image data and the respective first and/or second image data. Identified changes can then be subsequently analyzed as appropriate.

As described above, the magnetic resonance imaging scanner 10 can be utilized to perform any of the first, second, or third, scanning processes. However, it is also envisaged that different magnetic resonance imaging scanners can be utilized to perform at least the first and second scanning process. In particular, given that use of the first image data to determine one or more parameters of the second scanning process enables a volume of data required to be obtained by the second scanning process to be reduced, and hence enables use of a lower quality imaging scan in the second scanning process, a lower quality or less capable magnetic resonance imaging scanner can be utilized to perform the second scanning process.

Figure 4:
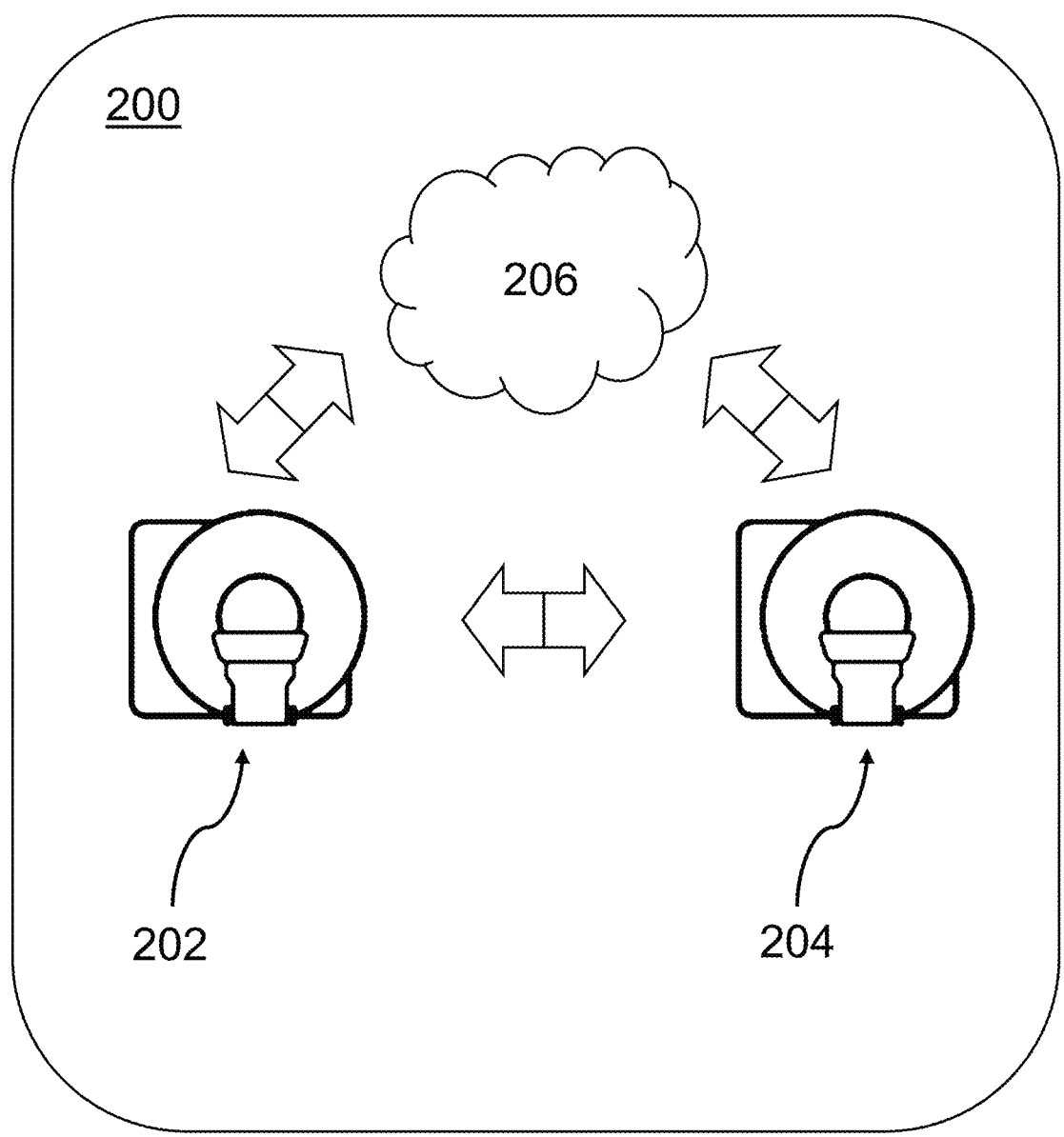
FIG. 4 is a schematic view of a system according to the present disclosure.

A system 200 in accordance with the present disclosure is illustrated schematically in FIG. 4.

The system 200 comprises a first magnetic resonance imaging scanner 202 capable of performing a relatively high quality imaging scan, and a second magnetic resonance imaging scanner 204 capable of performing a relatively low quality imaging scan. In some aspects, the first magnetic resonance imaging scanner 202 comprises the magnetic resonance imaging scanner 10 illustrated in FIG. 1. In some aspects, both the first 202 and second 204 magnetic resonance imaging scanners have a similar overall structure to the magnetic resonance imaging scanner 10 illustrated in FIG. 1, with components of the second magnetic resonance imaging scanner 204 having reduced capability relative to corresponding components of the first magnetic resonance imaging scanner 202. In some aspects, the second magnetic resonance imaging scanner comprises any one or more of a reduced magnetic field strength relative to the first magnetic resonance imaging scanner, a reduced field of view relative to the first magnetic resonance imaging scanner, a reduced signal-to-noise ratio relative to the first magnetic resonance imaging scanner, and a reduced spatial resolution relative to the first magnetic resonance imaging scanner.

The first 202 and second 204 magnetic resonance imaging scanners of the system 200 of FIG. 4 are in communication via the cloud 206.

Figure 3:
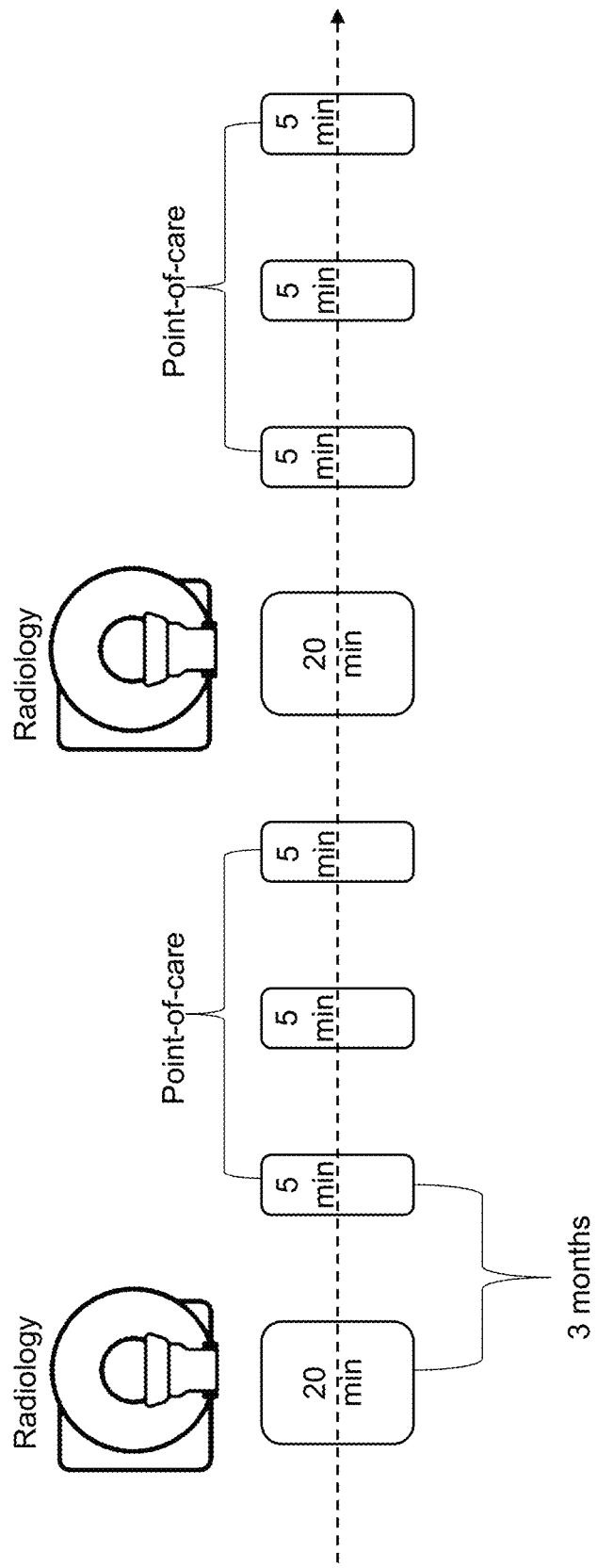
FIG. 3 is a schematic illustration of a longitudinal imaging study.
Figure 5:
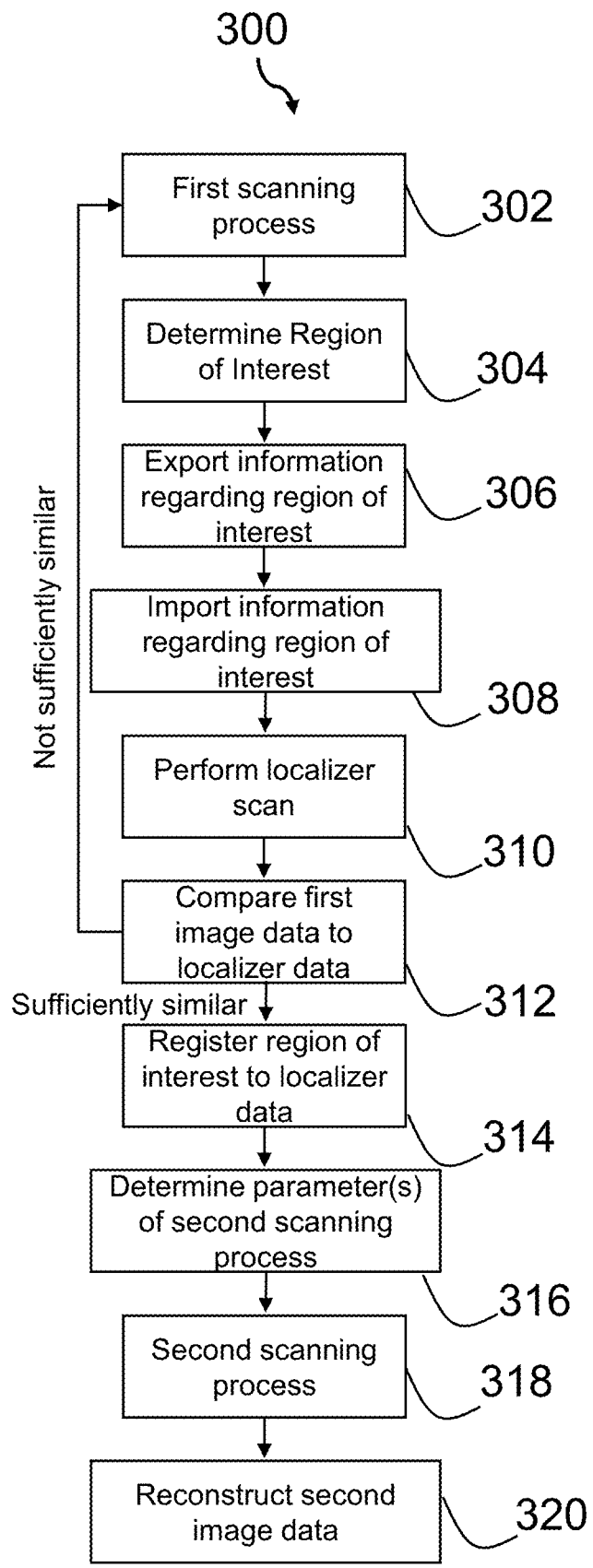
FIG. 5 is a flow diagram of a second method according to the present disclosure.

A first method 300 that utilizes the system 200 of FIG. 3 is illustrated in the flow diagram of FIG. 5.

The method 300 comprises scanning 302 a patient using the first magnetic resonance imaging scanner 202 in a first scanning process to obtain relatively high quality first image data.

The method 300 comprises, at the first magnetic resonance imaging scanner, determining 304 a region of interest in the relatively high quality first image data. In some aspects, determining the region of interest comprises any of performing segmentation, identifying landmarks, and identifying compartments/sub-compartments, in the manner previously described herein.

The method 300 comprises exporting 306 information regarding the determined region of interest, for example one or more of identified segments, landmarks and compartments, from the first magnetic resonance imaging scanner 202 in a generic data format. In some aspects, such information is exported to the cloud 206.

The method 300 comprises, at the second magnetic resonance imaging scanner 204, importing 308 the information regarding the determined region of interest. In some aspects, the information is imported from the cloud 206.

The method 300 comprises, at the second magnetic resonance imaging scanner 204, running 310 a localizer scan to obtain localization data, and comparing 312 the localization data to the relatively high quality first image data.

If the localization data is not sufficiently similar to the relatively high quality first image data, the method 300 comprises repeating the step of scanning 302 the patient using the first magnetic resonance imaging scanner 202.

If the localization data is sufficiently similar to the relatively high quality first image data, the method 300 comprises registering 314 the region of interest in the relatively high quality first image data to the localizer data. Any appropriate registration process may be utilized. Details of such registration processes are not pertinent to the present disclosure, and so will not be described here for sake of brevity.

The method 300 then comprises determining 316 one or more parameters of a second scanning process to be performed by the second magnetic resonance imaging scanner 204 based on the relatively high quality first image data, and also based on the specifications of the second magnetic resonance imaging scanner 204. In some aspects, the parameter of the second scanning process is determined to modify spatial encoding in the second scanning process. In some aspects, the parameter of the second scanning process is determined to modify a point spread function associated with the region of interest, for example according to the so-called "SLOOP" (spectral localization with optimal point spread function) method. In some aspects, the parameter of the second scanning process is determined to enable selective excitation during the second scanning process.

The method 300 comprises scanning 318 the patient in the second scanning process to obtain second relatively low quality image data, and reconstructing 320 the second image data using both the first relatively high quality image data obtained from the first magnetic resonance imaging scanner 202, and using a dataset relating to previously scanned patients. In some aspects, the dataset comprises relatively high quality imaging scans performed on previously scanned patients, as well as relatively low quality imaging scans performed on previously scanned patients.

Figure 6:
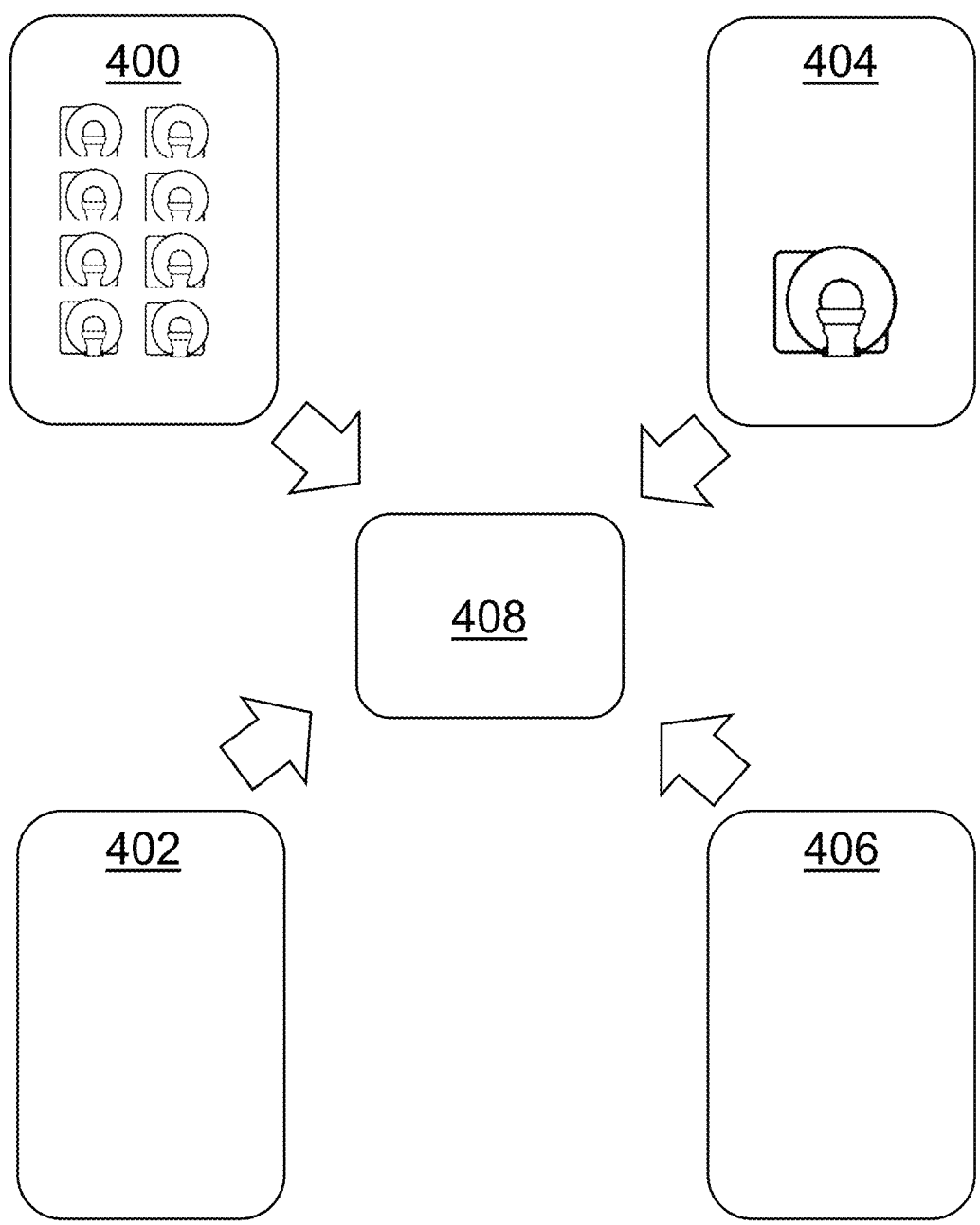
FIG. 6 is a schematic illustration of datasets used in a reconstruction process according to the present disclosure.

Such a reconstruction process is illustrated schematically in FIG. 6. Here any of a first dataset 400 comprising relatively high quality image data relating to previously scanned patients, a second dataset 402 comprising relatively low quality image data relating to previously scanned patients, a third dataset 404 comprising relatively high quality image data relating to the patient being scanned, and a fourth dataset 406 comprising relatively low quality image data relating to the patient being scanned, can be utilized to reconstruct further relatively low quality image data 408 relating to the patient being scanned. In such a manner, prior knowledge from previous scans can be used to reconstruct relatively sparse datasets. In some aspects, the third dataset 400 is obtained in the step of scanning 302 the patient using the first magnetic resonance imaging scanner 202 in the method 300.

Figure 7:
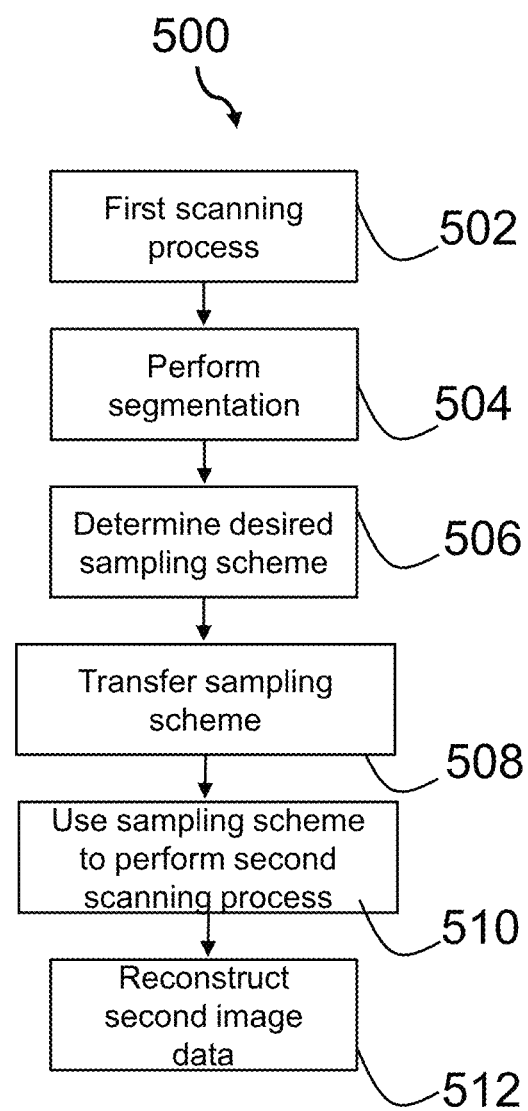
FIG. 7 is a flow diagram of a third method according to the present disclosure.

A second method 500 that utilizes the system 200 of FIG. 3 is illustrated in the flow diagram of FIG. 7.

The second method 500 comprises scanning 502 a patient using the first magnetic resonance imaging scanner 202 to obtain relatively high quality first image data.

The second method 500 comprises, at the first magnetic resonance imaging scanner 202, performing 504 segmentation of the prostate into anatomical and/or functional images and landmarks.

The second method 500 comprises, either in an edge environment of the first magnetic resonance imaging scanner 202 or in the cloud 206, determining 506 a desired sampling scheme based on the properties of the second magnetic resonance imaging scanner 204, a status of disease of the prostate of the patient, and the anatomical information determined in step 504.

The method 500 comprises transferring 508 the desired sampling scheme to the second magnetic resonance imaging scanner 204, and using 510 the desired sampling scheme, which can include any of a sub-sampled k-space in phase encoding, partition encoding optimization within compartment spatial response function, or a weighted combination of send or receive coil sensitivities, to scan the patient to obtain relatively low quality second image data.

The method 500 comprises reconstructing 512 the second image data, and in some aspects comprises using both the first relatively high quality image data obtained from the first magnetic resonance imaging scanner 202, and using a dataset relating to previously scanned patients.

In the first method 300 of FIG. 5 and the second method 500 of FIG. 7, it will be appreciated that a variety of processing steps can be performed in the cloud 206 in accordance with some aspects of the disclosure. For example, identification of regions of interest in the first image data, such as by segmentation or landmark identification, can take place in the cloud 206. Reconstruction processes can take place in the cloud 206, as can determining 506 a desired sampling scheme, and comparing 312 the localization data to the relatively high quality first image data. Data from any of the scans performed can also be stored in the cloud 206, and used for determining scanning strategy for subsequent scanning processes.

Use of the system 200 comprising the first magnetic resonance imaging scanner 202 and the second magnetic resonance imaging scanner 204 may find particular utility when the second image data and/or a reconstruction of the second image data is used in real-time as part of a guided treatment process, as previously described. In particular, the system 200 may find particular utility as part of a magnetic resonance guided radiotherapy system.

Magnetic resonance guided radiotherapy typically involves aiming to track a target volume motion or deformation and adapt radiotherapy in real-time. In using the system 200, significant information about the patient's anatomy is already available from scanning the patient using the first magnetic resonance imaging scanner 202, and that information could be used along with lower quality information subsequently obtained using the second magnetic resonance imaging scanner 204 to perform real-time tracking of the target volume, or measuring deformation of target volume. One of the challenges of magnetic resonance guided radiotherapy is the effect of magnetic fields from the magnetic resonance imaging processes on the radiotherapy beam. With the methods disclosed herein, a lower strength field magnet can be used in the second magnetic resonance imaging scanner 204, whilst still being able to provide the real-time position or deformation of the target volume with sufficient detail to the radiotherapy system.

Figure 8:
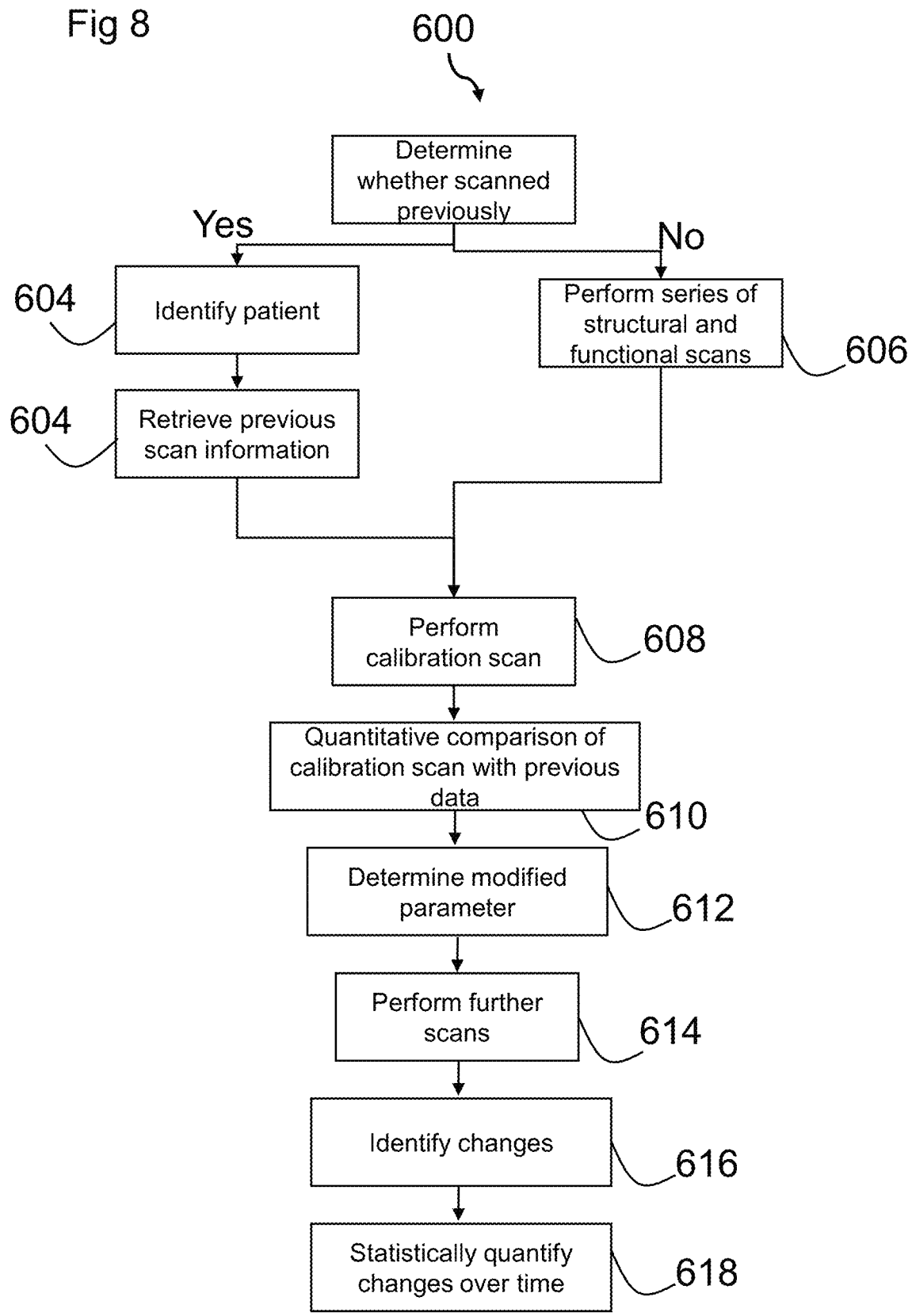
FIG. 8 is a flow diagram of a fourth method according to the present disclosure.

A further method 600 in accordance with the present disclosure is illustrated in the flow diagram of FIG. 8.

The method 600 comprises determining 602 whether a patient has been scanned previously. If the patient has previously been scanned, the method 600 comprises identifying 602 the patient via a patient ID, and retrieving 604 previous scan information for the patient. If the patient has not previously been scanned, then the method 600 comprises performing 606 a series of structural and functional scans.

The method 600 then comprises performing 608, using a magnetic resonance imaging scanner, a calibration scan to identify structural and functional changes compared to previous scans. The method 600 then comprises, at the magnetic resonance imaging scanner, quantitatively comparing 610 the calibration scans with the previous data of the patient.

The method 600 comprises determining 612 a modified parameter of a scanning process, and performing 614 further scans to improve the sensitivity and specificity of measurements of change in structure and function.

The method 600 comprises, at the magnetic resonance imaging scanner, identifying 616 intended and unintended structural or functional changes, and statistically quantifying 618 the changes over time.

It will be recognized that certain aspects of the present disclosure are optional, and that individual aspects of the present disclosure may find utility in their own right. For example, use of a consistency metric as previously described is envisaged absent a difference in quality between first and second scanning processes.

Figure 9:
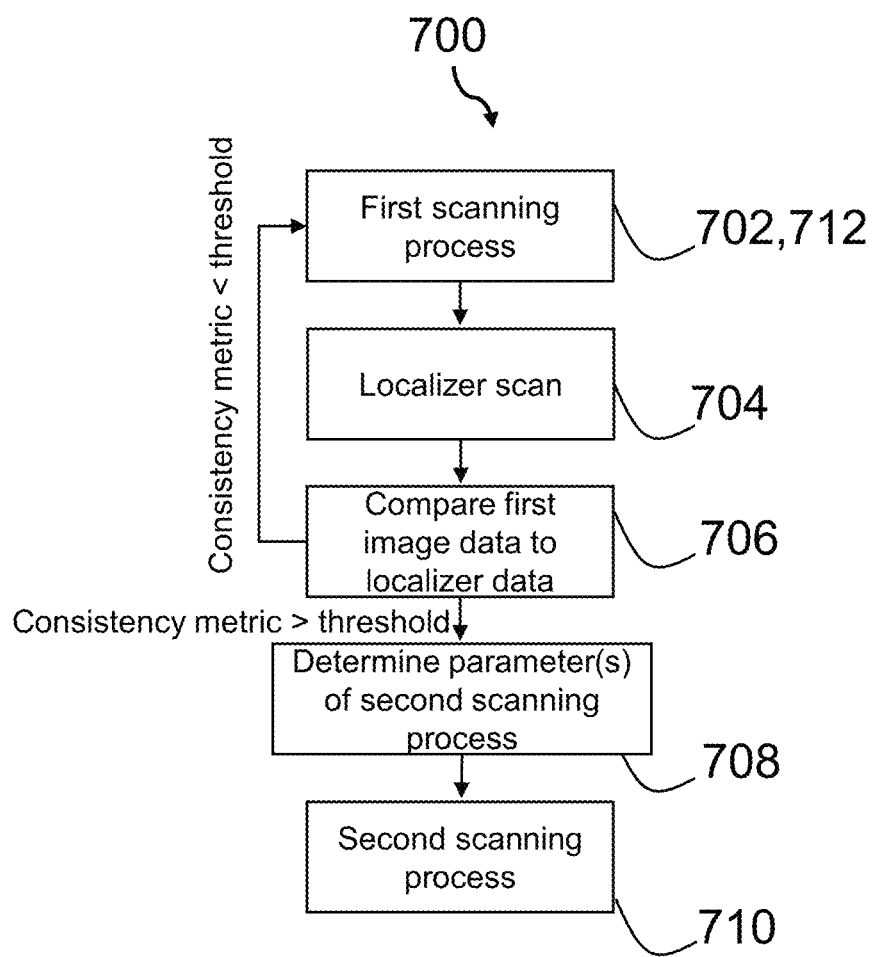
FIG. 9 is a flow diagram of a fifth method according to the present disclosure.

Thus a further method 700 in accordance with the present disclosure is illustrated in the flow diagram of FIG. 9.

The method 700 comprises scanning 702 the patient in a first scanning process to obtain first image data, and scanning 704 the patient in a localizing scanning process to obtain localizer data.

The method 700 comprises comparing 706 the first image data to the localizer data to determine a consistency metric between the first image data and the localizer data.

When the consistency metric is above a threshold value, the method 700 comprises determining 708, based on the first image data, one or more parameters of a second scanning process to be performed on the patient, and scanning 710 the patient in the second scanning process to obtain second image data. When the consistency metric is below the threshold value, the method 700 comprises scanning 712 the patient in a re-scanning process comprising a quality of imaging scan substantially similar to a quality of imaging scan, to obtain updated first image data.

Aspects discussed herein can provide improved efficiency for a longitudinal imaging study, and can facilitate at least some scans of a longitudinal imaging study taking place as part of point-of-care testing.

Independent of the grammatical term usage, individuals with male, female or other gender identities are included within the term.

Reference is made to the fact that the described methods and the described systems are merely preferred example aspects of the disclosure and that the invention can be varied by a person skilled in the art, without departing from the scope of the invention provided it is specified by the claims.

The invention claimed is:

1. A method of scanning an organ structure of a patient using magnetic resonance imaging, the method comprising:
scanning, in a first scanning process, the patient to obtain first image data indicative of at least the organ structure of the patient;
performing a localizer scan on the patient to obtain localizer data;
comparing the first image data to the localizer data to determine a consistency metric between the first image data and the localizer data;
when the consistency metric is above a threshold value, determining, based on the first image data, one or more parameters of a second scanning process to be performed on the patient, and
scanning the patient in the second scanning process to obtain second image data indicative of at least the organ structure of the patient,
wherein the first scanning process comprises a first quality of imaging scan, the second scanning process comprises a second quality of imaging scan, and the first quality of imaging scan is higher than the second quality of imaging scan; and
when the consistency metric is below the threshold value, scanning the patient in a re-scanning process comprising a quality of imaging scan similar to the first quality of imaging scan to obtain updated first image data indicative of at least the organ structure of the patient.

2. The method of claim 1, wherein the first scanning process is performed using a first magnetic resonance imaging scanner, and a second magnetic resonance imaging process is performed using a second magnetic resonance imaging scanner different to the first magnetic resonance imaging scanner.

3. The method of claim 2, further comprising:
determining, based on a property of the second magnetic resonance imaging scanner, one or more parameters of the second scanning process.

4. The method of claim 1, wherein the first quality of imaging scan comprises any one or more of a greater spatial resolution than the second quality of imaging scan, a greater signal-to-noise ratio than the second quality of imaging scan, a greater imaging volume than the second quality of imaging scan, a lower slice thickness to be resolved than the second quality of imaging scan, and high-sample recording of nuclear magnetic resonances compared to the second quality of imaging scan.

5. The method of claim 1, further comprising:
determining a region of interest in the first image data; and
determining, based on the determined region of interest, the one or more parameters of the second scanning process.

6. The method of claim 5, wherein determining the region of interest comprises performing a segmentation process on the first image data.

7. The method of claim 5, wherein determining the region of interest comprises identifying at least one of a landmark in the first image data and a sub-compartment in the first image data.

8. The method of claim 5, wherein determining the one or more parameters of the second scanning process comprises determining the one or more parameters of the second scanning process to modify a point spread function associated with the region of interest.

9. The method of claim 1, wherein determining the one or more parameters of the second scanning process comprises determining the one or more parameters of the second scanning process to modify spatial encoding in the second scanning process.

10. The method of claim 1, further comprising:
reconstructing the second image data based on any one or more of the first image data and a dataset comprising data relating to previously scanned patients.

11. The method of claim 1, further comprising:
determining, based on at least one of the first image data and the second image data, one or more parameter of a third scanning process to be performed on the patient; and
scanning the patient in the third scanning process to obtain third image data indicative of at least the organ structure of the patient.

12. A magnetic resonance imaging system, comprising:
a first magnetic resonance imaging scanner operable to obtain, as part of a first scanning process, first image data indicative of at least an organ structure of a patient, the first magnetic resonance imaging scanner operable to perform a first quality of imaging scan in the first scanning process;
a second magnetic resonance imaging scanner different from the first magnetic resonance imaging scanner, the second magnetic resonance imaging scanner operable to obtain, as part of a second scanning process, second image data indicative of at least the organ structure of the patient, and operable to perform a second quality of imaging scan in the second scanning process; and
a processor operable to determine, based on the first image data, one or more parameters of the second scanning process,
wherein the first quality of imaging scan is higher than the second quality of imaging scan, and
wherein the magnetic resonance imaging system is operable to determine and/or adjust a parameter of the first scanning process based on a property of the second magnetic resonance imaging scanner.

* * * * *